(12) United States Patent
Hagberg et al.

(10) Patent No.: US 9,000,196 B2
(45) Date of Patent: Apr. 7, 2015

(54) MAKING EPOXIDIZED ESTERS FROM EPOXIDIZED NATURAL FATS AND OILS

(71) Applicant: Archer Daniels Midland Company, Decatur, IL (US)

(72) Inventors: Erik Hagberg, Decatur, IL (US); Stephen Howard, Sherman, IL (US); George Poppe, Longs, SC (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/350,590

(22) PCT Filed: Oct. 17, 2012

(86) PCT No.: PCT/US2012/060497
§ 371 (c)(1),
(2) Date: Apr. 9, 2014

(87) PCT Pub. No.: WO2013/059238
PCT Pub. Date: Apr. 25, 2013

(65) Prior Publication Data
US 2014/0249322 A1 Sep. 4, 2014

Related U.S. Application Data

(60) Provisional application No. 61/548,757, filed on Oct. 19, 2011.

(51) Int. Cl.
*C07D 301/00* (2006.01)
*C07D 303/42* (2006.01)

(52) U.S. Cl.
CPC ............ *C07D 301/00* (2013.01); *C07D 303/42* (2013.01)

(58) Field of Classification Search
CPC ...................................................... C07D 301/00
USPC ........................................................... 549/513
See application file for complete search history.

(56) References Cited

U.S. PATENT DOCUMENTS 2,978,463 A * 4/1961 Kuester et al. ................ 549/539
2010/0010127 A1 * 1/2010 Barki et al. ................... 524/114

* cited by examiner

*Primary Examiner* — Taofiq A Solola
(74) *Attorney, Agent, or Firm* — William B. Miller

(57) ABSTRACT

Processes are described for making epoxidized fatty acid esters from epoxidized natural fats and oils, wherein low moisture fats and oils are identified and selected or made and used in a transesterification process. The products undergo phase separation, and reduced molar excesses of alcohol may be employed compared to processes not employing a low moisture feedstock.

10 Claims, No Drawings

MAKING EPOXIDIZED ESTERS FROM EPOXIDIZED NATURAL FATS AND OILS

The present invention is concerned with processes for making epoxidized fatty acid esters from various animal fats and plant oils.

Such epoxidized fatty acid esters have lately been of considerable interest for use as renewable source-based or—derived plasticizers for various polymer compositions and end uses. In particular, such materials have been investigated for use in polyvinyl halide compositions.

Polyvinyl chloride (PVC), the most common vinyl halide polymer, finds commercial application in a rigid, substantially unplasticized form and in a plasticized PVC form. Rigid PVC is used for pipework, ducts and the like in which high chemical resistance is needed but not flexibility or pliability. Plasticized PVC, on the other hand, finds application in films, sheeting, wire and cable coverings, moldings, conveyor belting, toys and hose, in addition to serving as a leather substitute and as a fabric covering for upholstered furniture, automotive seating and other articles.

Broadly speaking, plasticizers are materials which are combined with polymers such as polyvinyl chloride (hereinafter, PVC) to impart flexibility, extensibility and workability or some combination of these attributes to the polymer, as needed for a particular end use. Frequently, a combination of primary and secondary plasticizers is used, with the secondary plasticizers not acting in and of themselves to impart the desired attributes to the PVC but serving to improve the effectiveness of the primary plasticizer(s) and optionally offering other characteristics to a PVC composition in which the materials are incorporated.

Historically, the majority of primary PVC plasticizers have been petroleum-derived phthalates and benzoate compounds, dioctyl phthalate and diisononyl phthalate being notable examples. However, such petroleum-derived plasticizers are frequently expensive to produce and use because of fluctuations in the pricing and availability of petroleum, and are increasingly likely to remain so as petroleum reserves are reduced and new supplies prove more costly and difficult to secure. Further, certain of the petroleum-derived phthalate plasticizers have raised concerns for their potential to disrupt human endocrine activity, and regulatory controls have been established in a number of countries to address these concerns.

Unmodified plant/vegetable oils are largely incompatible with PVC resin, but certain modified derivatives of such oils, such as epoxidized soybean oil (ESO), are compatible with PVC resin and have been actively investigated for use as a lower cost, renewable source-based alternative to the petroleum-based plasticizers, both as primary and secondary plasticizers. The interest in developing useful plasticizers from renewable sources, such as animal fats or especially plant/vegetable oils, has developed partly also from the expectation that such materials would be less likely to cause physiological disturbances or other injuries to persons coming into contact with products which require plasticizers in their composition.

As related in U.S. Pat. No. 6,797,753 to Benecke et al., however, these modified vegetable oil derivatives had been used to a limited extent commercially as secondary plasticizers only, because of compatibility limitations in PVC. Benecke et al. and others accordingly sought to identify further modifications or other vegetable oil-derived materials with improved compatibility for use as a primary plasticizer, while retaining the beneficial thermal stabilization properties of epoxidized soybean oil. In Benecke et al., primary plasticizers are reported where the plasticizers contain fatty acids derived from vegetable oils and the fatty acids are substantially fully esterified with an alcohol (monool or polyol), the fatty acids have unsaturated bonds that are substantially fully epoxidized, and the fatty acids are added substantially randomly to one or more hydroxyl sites on the alcohol. Primary plasticizers particularly mentioned include epoxidized pentaerythritol tetrasoyate, epoxidized propylene glycol disoyate, epoxidized ethylene glycol disoyate, epoxidized methyl soyate, epoxidized sucrose octasoyate and the epoxidized product of soybean oil interesterified with linseed oil.

Benecke et al. describe several methods by which these plasticizers may be made. In one embodiment, found at column 3, lines 17-30 of the '753 patent, the vegetable oil fatty acids are linked by direct esterification to monoalcohols or polyalcohols, and the esterified products are then epoxidized. In a second embodiment described starting at line 30, the direct esterification step is replaced with transesterification, whereby the monool or polyol reacts with a lower alkyl ester of a vegetable oil fatty acid to produce the desired ester plus a lower alcohol, and the ester is then epoxidized. In yet another embodiment, a first ester is interesterified with a second ester, and the desired ester is again epoxidized.

WO 2009/102877A1, published Aug. 20, 2009 for "A Replacement Plasticizer System for Phthalate-Plasticized Formulations", is similarly directed, describing epoxidized fatty acid esters useful as primary plasticizers in a phthalate-free system and which are suitably nonvolatile, not petroleum-based, and capable of imparting thermal stability to formulations presently using phthalate plasticizers, including those based on PVC, other halogenated polymers, acid-functionalized polymers, anhydride-functionalized polymers, and nitrile rubbers. Suitable epoxidized fatty acid ester plasticizers are said to include epoxidized biodiesel (conventionally, fatty acid methyl esters of soy, rapeseed or palm oils, though $C_1$-$C_{14}$ esters are more generally contemplated) and epoxidized derivatives of fatty acid esters of biodiesel. Methods described for making the epoxidized fatty acid esters, as in Benecke et al., involve formation of the fatty acid ester first, followed by epoxidation of the ester.

Epoxidized methyl soyate esters—as prominently featured in both Benecke et al. and the WO'877 application just discussed—have also been known to be made starting from epoxidized soybean oil by alcoholysis, see U.S. Pat. No. 3,070,608 to Kuester et al. (hereinafter, Kuester et al.), for example, wherein ESO (epoxidized soybean oil) is reacted with a molar excess of methanol in the presence of sodium methoxide as a catalyst, to produce EMS. The total epoxide content in going from ESO to EMS is indicated at column 1, lines 21-22, as being relatively unchanged, showing "little or no decrease".

Commonly-assigned, copending U.S. Provisional Patent Application Ser. No. 61/501,312, filed Jun. 27, 2011 for "Reduced Color Epoxidized Esters from Epoxidized Natural Fats and Oils", very recently found that reduced color epoxidized fatty acid esters (such as EMS) could be made from an epoxidized natural fat or oil (such as ESO) through the inclusion of borohydride in either a transesterification process or in an interesterification process.

As well, it was determined that the addition of the borohydride and starting from an epoxidized natural fat or oil appeared not to detract in any material way from the other commercially-relevant performance attributes of a plasticized polymer composition incorporating such a reduced color epoxidized fatty acid ester, as compared to an equivalent composition prepared using an epoxidized fatty acid ester made according to the known methods of Benecke et al. or the WO'877 application.

Given the indication in the WO'877 application that "epoxides made from esters of fatty acids such as the epoxidized methyl ester of soy oil are too volatile to serve as useful plasticizers of PVC," pg. 1, lines 30-31, this was a finding of considerable significance for the specific reduced color epoxidized fatty acid ester, epoxidized methyl soyate or EMS. Rather than being dependent on the production economics or availability of biodiesel, which are in turn to some extent dependent on fuels demand, pricing and usage patterns, epoxidized methyl soyate esters could be made with an available supply of epoxidized soybean oil—the supply and demand for which is at least to some extent related to demand for the same plasticized PVC compositions in which ESO can be used as a secondary plasticizer and thermal stabilizer, and not to conditions in the fuel markets.

Moreover, the capacity to make EMS and other epoxidized soybean oil ester derivatives from ESO is advantageous also, in the fact that the same ESO that would be used as the feed for making the EMS may also be combined with the these products in the traditional role of ESO, as a secondary plasticizer and thermal stabilizer—so that the ESO may be both a feed for an effective, biobased primary plasticizer in EMS and in combination with EMS provide an entirely renewable source-based, phthalate-free plasticizer system offering.

On the other hand, a comparative disadvantage of making EMS from already epoxidized soybean oil rather than from regular, unepoxidized soybean oil—of transesterifying after epoxidizing, rather than the reverse—was that, in the absence of the further improvements offered by the present invention, the route through ESO was found in the copending '312 provisional to require much larger molar excesses of methanol as compared to starting from unepoxidized soybean oil to make the methyl soyate ester material, and then epoxidizing the ester to make EMS plasticizer. For example, in a typical biodiesel process, from 5 to 8 molar equivalents of methanol are needed to drive the transesterification reaction to completion, whereas in the process of the copending '312 provisional application, more than twice the amount of methanol was initially needed (e.g., on the order of twenty or more molar equivalents of methanol).

In particular, it was observed that while in the biodiesel process the transesterification products resolve into two phases, with the byproduct glycerol separating out from the methyl soyate esters into respective glycerol and ester phases, the transesterification of ESO in the copending '312 provisional application provided but a single phase product. The removal of the byproduct glycerol in the biodiesel process into a distinct phase functions to drive the transesterification reaction equilibrium to the right, to the product side. The consequence in the ESO-derived process of the copending '312 provisional application was that, in the absence of a similar phase separation, a larger molar excess of the methanol reactant was thus required to comparably shift the equilibrium and drive the reaction to completion.

As mentioned previously, Kuester et al. also disclosed making EMS from already-epoxidized soybean oil. Interestingly, Kuester et al. describe using molar excesses of methanol in line with those used in a biodiesel process, namely, "preferably five or more" (U.S. Pat. No. 3,070,608 at col. 1, line 56). While "five or more" certainly embraces the high molar excess requirements we observed, the examples reported by Kuester et al. expressly reference phase separation's occurring in their products—so that evidently Kuester et al.'s transesterification of ESO with methanol differed in some undisclosed way, to provide the desired phase separation behavior and enable the lower methanol excesses to be used.

The present invention relates in one aspect to a process for making epoxidized fatty acid esters from epoxidized natural fats and oils by determining the moisture content of one or more epoxidized natural fats or oils, selecting a low moisture epoxidized natural fat or oil for use, then carrying out a transesterification of the selected low moisture epoxidized natural fat or oil with an alcohol in the presence of a transesterification catalyst and under conditions which are effective for carrying out the transesterification reaction, whereby the resultant product mixture phase-separates into an epoxidized fatty acid ester phase and a second phase comprising byproduct glycerol.

In another aspect, the present invention concerns a process for making epoxidized fatty acid esters from epoxidized natural fats and oils, by first making a low moisture epoxidized natural fat or oil feedstock, then carrying out a transesterification of the selected low moisture epoxidized natural fat or oil with an alcohol in the presence of a transesterification catalyst and under conditions which are effective for carrying out the transesterification reaction, whereby the resultant product mixture phase-separates into an epoxidized fatty acid ester phase and a second phase comprising byproduct glycerol.

In considering the single phase phenomenon, it was appreciated that with the various commercially-obtained epoxidized soybean oils evaluated the moisture content of the oils was typically quite high, for example, on the order of 0.5 percent by weight. We found that when these same epoxidized soybean oils were dried, the product mixture did undergo phase separation into the desired epoxidized fatty acid ester, product phase and a byproduct glycerol phase, so that to achieve complete conversion—defined for present purposes as 98% or greater conversion to the ester from the epoxidized natural fat or oil—not more than about 8 molar excesses of methanol were required.

It has been appreciated for some time, of course, that various epoxidized natural fats and oils, for example, epoxidized soybean oil, can have differing water contents in their commercially-available forms. As well, it has been appreciated that excessive moisture in the additives for a flexible PVC formulation, such as, for example, an epoxidized natural fat or oil added as a secondary plasticizer, can create certain difficulties in compounding or over time—for example, hydrolysis of PVC formulation additives, exudation, haze and even moisture-induced porosity in extrudates. Accordingly, epoxidized soybean oils often have moisture content specified as a parameter, and methods have been published in the literature for drying epoxidized natural fats and oils. However, to our knowledge, the effect of moisture content of the epoxidized natural fat or oil on phase separation behavior of the products of a transesterification process involving the epoxidized natural fat or oil and an alcohol has not been appreciated.

Thus, in one aspect the present invention concerns a process for making epoxidized fatty acid esters from epoxidized natural fats and oils by determining the moisture content of one or more epoxidized natural fats or oils, selecting a low moisture epoxidized natural fat or oil for use, then carrying out a transesterification of the selected low moisture epoxidized natural fat or oil with an alcohol in the presence of a transesterification catalyst and under conditions which are effective for carrying out the transesterification reaction, whereby the resultant product mixture phase-separates into an epoxidized fatty acid ester phase and a second phase comprising byproduct glycerol.

"Low moisture" in the context of the present invention, it should be noted, means only that the moisture content of the epoxidized natural fat or oil is sufficiently low that the transesterification products will phase separate with time. The degree of "dryness" necessary for a given epoxidized natural fat or oil can be expected to vary somewhat for different epoxidized natural fats and oils, different alcohols or combinations of alcohols, varying transesterification conditions etc., but as a general guideline we expect that the moisture content should ordinarily be 0.5 percent by weight or less, preferably 0.25 percent by weight or less and more preferably 0.1 percent by weight or less, as determined by Karl Fischer titration analysis or by any other conventionally practiced measurement method. These moisture contents, it should be noted, generally correspond to those we expect should be suitable given the use of alcohols which are similarly "dry", for example, containing 2500 ppm by weight or less of water, and preferably 1000 ppm by weight or less as used in the examples which follow.

The required low moisture contents may be found in certain epoxidized natural fats or oils without any requirement for further drying to occur. However, other epoxidized natural fats or oils may be found to have excessive moisture, for example, through prolonged exposure to humid storage environments or through other causes, and will need to undergo a drying step in order to provide the desired phase separation of the transesterification products. In the alternative, an epoxidized natural fat or oil having the requisite low moisture content can be made as needed, rather than or in addition to drying a preexistent epoxidized natural fat or oil supply that has been found to contain too much moisture. As well, a low moisture epoxidized natural fat or oil feedstock can be made merely by blending epoxidized natural fats and oils of varying higher and lower moisture contents, to achieve a blended product that qualifies as a low moisture epoxidized natural fat or oil.

Accordingly, in another embodiment of the present invention, a process is provided for making epoxidized fatty acid esters from epoxidized natural fats and oils, by first making a low moisture epoxidized natural fat or oil feedstock, then carrying out a transesterification of the selected low moisture epoxidized natural fat or oil with an alcohol in the presence of a transesterification catalyst and under conditions which are effective for carrying out the transesterification reaction, whereby the resultant product mixture phase-separates into an epoxidized fatty acid ester phase and a second phase comprising byproduct glycerol.

As already mentioned, various methods have been published in the literature for drying epoxidized natural fats and oils. Any of the methods that have been found suitable for drying the fats and oils to an extent whereby these fats and oils would properly be characterized as "low moisture" can be used, but an example would involve exposing the epoxidized natural fat or oil to temperatures in the range of from 90 degrees Celsius to 130 degrees Celsius for from 30 to 60 minutes, under high vacuum conditions. A drying method of this general character is described in U.S. Pat. No. 2,978,463 to Kuester et al.

Other aspects of the transesterification processes contemplated by the present invention are in keeping with conventional practice, or in relation to the reduced color transesterification methods described in commonly-assigned, copending U.S. Provisional Patent Application Ser. No. 61/501,312, filed Jun. 27, 2011 for "Reduced Color Epoxidized Esters from Epoxidized Natural Fats and Oils", are as described therein.

A detailed treatment of these other aspects is consequently not required. In general, however, the epoxidized natural fat or oil itself can be derived from animal or plant (including vegetable) sources. Preferably the epoxidized natural fat or oil is a vegetable or seed oil, for example, genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof. Preferably, the oil is a polyunsaturated oil selected from the group above. Most preferably, the polyunsaturated oil is low in C18:3 or higher fatty acids. Although any polyunsaturated oil that has sufficiently low levels of C18:3 or higher fatty acids is suitable for the present method, preferably, the oil is safflower oil, sunflower oil or corn oil. Preferred oils contain less than about 2 percent of C18:3 or higher polyunsaturated fatty acids. More preferably, the oils contain less than 1 percent of C18:3 or higher polyunsaturated fatty acids. Also preferred are polyunsaturated oils containing less than 2 percent linolenic acid. More preferably, the linolenic content is less than 1 percent.

The alcohol reactant for the transesterification may broadly be selected from any of the wide variety of aliphatic or cyclic monohydric, dihydric or polyhydric alcohols that will form an epoxidized fatty acid ester with the epoxidized natural fats or oils in the presence of a transesterification catalyst, though aromatic alcohols are less preferred. As demonstrated by Kuester et al., unsubstituted aliphatic alcohols as well as amine substituted aliphatic alcohols having an amine group with no reactive hydrogens on the amine nitrogen may also be considered, triethanolamine being an example of the latter. Monohydric aliphatic alcohols having from 1-20 carbon atoms are preferred, and while primary, secondary and tertiary alcohols may be considered, primary monohydric aliphatic alcohols are more preferred. Methyl, ethyl and benzyl primary monohydric aliphatic alcohols are particularly preferred.

The catalyst can be any catalyst that is suited for carrying out the transesterification reaction, and a number of such catalysts are known. Preferably, the catalyst used in the present process is an alkaline catalyst. More preferably, the catalyst is selected from the group consisting of sodium methoxide, sodium ethoxide, potassium methoxide, potassium ethoxide, potassium tert-butoxide or an N-heterocyclic carbene catalyst such as 1,3-Bis(2,6-diisopropylphenyl)imidazol-2-ylidene (CAS 244187-81-3), from Sigma-Aldrich Co. (though other N-carbene catalysts and preparation methods will be within the capabilities of those skilled in the art without undue experimentation). Most preferably, the catalyst used in the present process is sodium methoxide.

While the observed, phase-separation effects of using a low moisture epoxidized natural fat or oil were initially seen in the context of the reduced color transesterification process described in the commonly-assigned, copending '312 provisional application, the present invention is not limited to that particular context of use but can be applied to transesterifications conducted in the absence of borohydride.

Where reduced Pt/Co color materials are desired, however, a preferred embodiment would use the low moisture epoxidized natural fats and oils with borohydride as taught in the incorporated '312 provisional application, wherein borohydride is included for a preferred embodiment in a transesterification reaction mixture with the low moisture epoxidized natural fat or oil and alcohol before a transesterification catalyst is introduced, though other embodiments are described wherein the borohydride and the catalyst are concurrently or substantially concurrently incorporated in the reaction mixture with the epoxidized natural fat or oil and alcohol and wherein borohydride is incorporated in the reaction mixture both prior to and concurrently with the introduction of the catalyst.

In any of these modes of incorporating borohydride into the transesterification process, the borohydride material can be selected from the group consisting of sodium borohydride, potassium borohydride and lithium borohydride. By routine experimentation, a skilled artisan will quickly be able to determine the amount of borohydride that will produce a particular reduction in color, and whether additional known color removal techniques (for example, the use of carbon treatment or bleaching) are desirably used. Preferably, the borohydride is present in an amount between 1.0 percent and 0.0001 percent by weight of the reactants and catalyst. More preferably, the amount of borohydride is between 0.1 percent and 0.001 percent. The catalyst in any event preferably comprises a greater part of the reaction mixture as compared to the borohydride, as greater amounts of borohydride can (as more fully described in the '312 application) tend to inhibit the desired transesterification process without a corresponding degree of further improvement in the Pt—Co color of the product, or under circumstances where further improvements in the Pt—Co color are not really needed.

A pretreatment of the borohydride as exemplified in the '312 application may also be employed, whereby the borohydride is combined with diglyme (diethylene glycol dimethyl ether) in solution for a time before being combined with the catalyst.

In terms of the process conditions used, the combined low moisture epoxidized natural fat or oil and alcohol are heated in the presence of the transesterification catalyst (and borohydride, for certain reduced Pt/Co color applications) to effect a transesterification of the low moisture epoxidized natural fat or oil. Preferably, the combined starting materials are heated to a temperature between 40° C. and 70° C. under a slight vacuum in an inert atmosphere, such as N2, Ar or CO2. More preferably, the temperature range is from 40° C. to 55° C. The reactants are preferably used neat and the reaction is carried out in the substantial absence of moisture from other sources than the low moisture epoxidized natural fats and oils, with continuous agitation. It is preferred that the atmosphere is free of O2 and is composed of an inert gas such as those listed above. The combined mixture is heated slowly to the above temperature range. During the process of transesterification, the temperature is maintained in the above range until a certain conversion to product has occurred. In one embodiment exemplified below, at one or more intermediate stages short of full conversion, additional alcohol and catalyst (and additional borohydride, if optionally used) can be added for one or more further stages of reaction leading toward a substantially full to full conversion of the low moisture epoxidized natural fat or oil feedstock. In another exemplified embodiment, the alcohol and catalyst (and optional borohydride) are incorporated in one stage, and the reaction continues with the initially incorporated materials until also substantially completed. The catalyst is in either basic embodiment then neutralized with acid, such as citric acid or phosphoric acid.

The resultant transesterification products may then be washed with preferably deionized water, and allowed to phase-separate in the manner of conventional fatty acid methyl ester, biodiesel practice (and as desired, in the same biodiesel product separation and purification equipment), into an epoxidized fatty acid ester product phase and a byproduct glycerol phase including substantially the wash water which was used. Alternatively, the resultant transesterification products can be allowed to phase-separate, and one or more washes are conducted on the product phase/previously washed product phase only rather than on a whole body of materials pre-separation. Residual water in an initial, intermediate washed and/or final washed product phase can be conventionally removed in one or more iterations by evaporation, for example, under vacuum (or reduced pressure) conditions in a rotary evaporator at elevated temperatures.

It will be appreciated by those of ordinary skill in the art, in view of the present teachings and of the teachings of the incorporated '312 application, that the transesterification of low moisture epoxidized natural fats and oils according to the present invention may be conducted in a batchwise, semi-batch or continuous manner, and likewise that the recovery and further processing of the transesterification products may be independently carried out in a batchwise, semi-batch or continuous manner.

The epoxidized esters of the present invention can be contemplated for use as primary or secondary plasticizers in a variety of polymers, including halogenated polymers, acid-functionalized polymers, anhydride-functionalized polymers, and nitrile rubbers. An exemplary halogenated polymer is a PVC polymer, where "PVC" or "polyvinyl chloride" as used herein is understood to cover the range of homo- and copolymers of vinyl chloride with typically up to 20% of comonomers such as vinyl acetate, propylene, ethylene, diethyl maleate, dimethyl fumarate and other ethylenically unsaturated comonomers. Examples of other halogenated polymers include polyvinyl halide polymers, chlorinated polyolefins and chlorinated rubbers. Suitable acid-functionalized polymers include acrylic acid-functionalized polymers, as well as acrylic and other polymers in need of plasticization to reduce glass transitions or improve toughness.

Where used as primary plasticizers, the epoxidized fatty acid esters can comprise preferably at least 20 percent by weight of a polymer composition, more preferably will comprise at least 30 percent by weight of a polymer composition, and most preferably will comprise at least 50 percent by weight of a polymer composition.

The plasticized polymer compositions contemplated by the present invention can be formulated, it is noted, in all other respects in a conventional manner, including various kinds of additives in addition to the epoxidized fatty acid esters of natural fats or oils. When the epoxidized esters are used in preferred embodiments as the primary plasticizers of a primary/secondary plasticizer system, for example, a renewably-based secondary plasticizer and thermal stabilizer can be added (such as, but without being limited thereto, the same, low moisture epoxidized natural fat or oil used for a feedstock to the transesterification process by which the epoxidized fatty acid esters were made), or other secondary plasticizers (including petroleum-based plasticizers) or other additives for improving one or more properties of heat stability, lubricity or weathering resistance, as ultraviolet absorbers, fillers, anti-oxidants, anti-static agents, anti-fogging agents, pigments, dyestuffs, crosslinking aids and the like can be incorporated in the compositions. The epoxidized esters may also be used in certain embodiments in combination with other primary plasticizers such as dioctylphthalate, other phthalates, citrates, benzoates, trimellitates, and other aliphatic diesters, though preferably the plasticized polymer compositions will not include any added phthalates and will include substantially only renewably-based or biobased plasticizers.

The present invention in its several related aspects is more particularly illustrated by the examples below:

EXAMPLE 1

A quantity of epoxidized soybean oil (Plas-Chek™ 775 epoxidized soybean oil from Ferro Corporation, Cleveland, Ohio) was dried by heating at 85 degrees Celsius under high vacuum for one hour, based on published literature conditions of typically 90 to 130 degrees Celsius under high vacuum for from 30 to 60 minutes.

In a 5 liter round bottom flask set up with a heating mantle and controller, stirrer and vacuum, we added 1300 grams of the dried ESO. A solution of 0.5 grams sodium borohydride in 30 grams of anhydrous methanol was added with stirring, followed by 200 grams additional of anhydrous methanol. A premix of 20 grams of 30% sodium methoxide in methanol and 1.3 grams of sodium borohydride were then added. Nitrogen was bubbled through the mixture with stirring, and the mixture was heated until a temperature of 45 degrees Celsius was reached. The mixture was held under nitrogen at 50 degrees Celsius for an hour to allow the transesterification reaction to occur. The flask's contents were transferred to a separatory funnel and allowed to separate for one hour, after which the lower byproduct glycerol layer (128 grams) was removed. The remainder was returned to the flask, and a premixed solution of 42 grams anhydrous methanol, 4 grams of 30% sodium methoxide and 0.3 grams of sodium borohydride was added. A second reaction step was conducted then at 50 degrees Celsius under nitrogen for 1.5 hours, checking reaction progress by NMR spectroscopy. The product was transferred again to a separatory funnel, and allowed to phase separate over an additional half hour. The lower byproduct glycerol layer (9.5 grams) was removed, and the top product layer was placed back in the reaction flask and neutralized with 50% citric acid solution in deionized water. After stirring, the product was washed with deionized water several times in a separatory funnel, then the remaining washed top product layer was dried over MgSO4 and filtered. The product was then stripped on a rotary evaporator. The stripped final product had a color of 35 on the Pt/Co Hazen solor scale, per ASTM D1209.

COMPARATIVE EXAMPLE 1

Example 1 was reproduced, except that the Plas-Chek™ 775 epoxidized soybean oil was not dried first. The reaction products did not phase separate.

EXAMPLE 2

For this example, a single reaction step was used rather than two steps as in Example 1. Drying of 1000 grams of Plas-Chek™ 775 epoxidized soybean oil was accomplished by heating the material to 85 degrees Celsius and holding for an hour. The dried ESO was added to a reactor and stirred under a blanket of nitrogen at 55 degrees Celsius. A solution of 1 g sodium borohydride in diglyme was added to the ESO in the reactor with stirring for one half hour, after which time 200 grams of anhydrous methanol and 3 grams of sodium methoxide in methanol were added. The reaction mixture was stirred for one hour at 55 degrees Celsius. The reaction products separated into two phases. The bottom phase was removed via separatory funnel. To the top layer was added a solution of 25 grams of citric acid in water. The mixture was stirred again at 55 degrees Celsius for two minutes, then allowed to phase separate again into two phases. The bottom phase was removed, and the top phase was washed twice with deionized water, allowing the water to phase separate from the epodized fatty acid ester product after each washing. Upon removal of the second water wash layer, the top phase was heated under vacuum to 85 degrees Celsius to remove any residual moisture.

EXAMPLE 3

One thousand grams of epoxidized soybean oil was dried by means of a rotary evaporator for 1 hour in a 90 degrees Celsius water bath. The dried ESO was added to a jacketed glass reactor along with 300 grams anhydrous methanol. The mixture was stirred at 55 degrees Celsius as a mixture of 1 gram sodium borohydride dissolved in a sodium methoxide (3 grams)/methanol (25 grams) solution was added. The reaction continued at 55 degrees with stirring for about 45 minutes, at which point a solution of about 10 grams citric acid in 30 mL of methanol was added. Excess methanol was removed under vacuum in the rotary evaporator. The reactor contents were then moved to a separatory funnel and allowed to phase-separate. The lower, glycerol-containing layer was removed as the top layer was washed with 300 milliliters of deionized water. After phase separation, the lower aqueous layer was removed, and the top epoxidized ester product layer was dried under vacuum on the rotary evaporator.

EXAMPLES 4 AND 5

For Examples 4 and 5, plasticized PVC compositions were prepared from the EMS product from Example 1 and from the EMS product prepared in Example 4, as well as from a "Control" EMS made using the transesterification method described in U.S. Pat. No. 6,797,753 to Benecke et al., beginning at column 3, line 30, and a subsequent conventional peroxide epoxidation. The "Control" PVC composition corresponding to the prior art method EMS and the PVC compositions for Examples 4 and 5 each were comprised of 100 parts by weight of Geon™ 121 AR homopolymer PVC dispersion resin from PolyOne, Inc., Avon Lake, Ohio, with 70 parts by weight of the EMS plasticizer in question, and 2 parts by weight of Therm-Chek™ LOHF 120 Ba/Zn stabilizer (Ferro, Inc., Cleveland Ohio). Weighed powdered solids were introduced to a 1-gallon mixing bowl. These materials were combined with stirring at the lowest speed of a 3-Speed Hobart Paddle Mixer, slowly adding liquid components to solid components. The contents were mixed for about 30 minutes, and the mixture was subjected to vacuum (such as in a large dessicator) to reduce air entrapment.

Several tests were carried out on the PVC compositions, according to the following protocols:

Paste Viscosity—The paste viscosity of a plastisol specimen describes the flow behavior of plastisols under low shear. The suitability of a dispersion resin for a given application depends on the viscosity characteristics of the plastisol and indicates performance in pouring, casting, molding, and dipping processes. The Paste Viscosity Test (Brookfield Viscosity Test) was carried out substantially according to ASTM procedure D1824 using a Brookfield RVFD Viscometer. Measurements were made at room temperature at 2 revolutions per minute (RPM) and 20 RPM. Low initial paste viscosity is desired for ease of handling, with preferably as little increase as possible over time, so that the paste viscosity measurements were repeated on several occasions over a period of 28 days to determine the stability of the paste viscosity of the plastisol specimens.

Air Release—The Air Release Test is carried out to determine the relative speed of release of entrained air from a plastisol. Liquid plastisol is poured into at 4 ounce polypropylene cup or equivalent and the plastisol is stirred vigorously with a spatula for one minute. As the entrapped air rises to the surface, the rate at which the bubbles break is observed and recorded. A relative rating of "Excellent" to "Poor" is assigned by comparison with reference formulations. "Excellent" air release (5 minutes) is obtained with a reference formulation comprising 100 parts Geon™ 121 AR resin, 67 parts diisononyl phthalate (DINP), 3 parts epoxidized soybean oil (ESO), and 2 parts Therm-Chek™ LOHF 120 stabilizer. "Poor" air release (more than 60 minutes) is obtained with a reference formulation comprising 100 parts Geon™ 121 AR resin, 67 parts benzyl butyl phthalate (BBP), 3 parts ESO, and 2 parts Therm-Chek™ LOHF 120 stabilizer.

Hardness—The Shore A Hardness test is carried out substantially according to ASTM D2240 using a Shore Durometer Gage to determine the hardness values of plastisols. Hardness is a measure of the efficiency of the plasticizer. At equal levels of incorporation of two different plasticizers in otherwise identical plastisols, the plasticizer yielding the softer plastisol is a more efficient plasticizer.

Heat Stability—The Metrastat Heat Stability test is used to measure the thermal stability of a plastisol film at high temperatures. Fused sheets of plastisols are prepared and exposed to high temperatures for varying time periods along the length of the strips. An excellent plastisol does not discolor or char and maintains flexibility after the test. Fused sheets of plastisol are prepared by "drawing down" plastisol onto a heat-stable surface (release substrate) using a 20 mil (0.020") drawing bar; the release substrate must be capable of withstanding at least 200° C. (390° F.) for 5 minutes. The fused sheets ("draw downs") are fused for 3 minutes in an oven at 200° C. (390° F.). Fused sheets are allowed to cool at room temperature for a minimum of 15 minutes before removing from the release substrate. Sample strips measuring 25 cm (9.75 inch) by 2.5 cm (1 inch) are cut from the fused sheets. A Metrastat™ oven is preheated to 191° C. (375° F.) and sample strips are placed onto the travelling tray of the Metrastat™ oven. A one hour exposure cycle is started. As the tray travels the sample strips are exposed to the oven temperature over a time gradient of 0-60 minutes. When the cycle is complete, sample strips are allowed to cool for 1 hour and mounted onto display paper which shows the time the sample was exposed to high heat.

Gelation—The gel curve and gelation temperature test is carried out to determine the viscosity of plastisols under increasing temperature with a CarriMed™ CSL-2 500 rheometer. The gelation temperature indicates the solvating power of the plasticizer; lower gelation temperatures indicate greater solvating power, and are preferred for convenience in applications such as screen printing, dip coating, and preparation of soft rubber compounds because less heat is needed to maintain low viscosity of the plastisols. The viscosity is plotted as a function of temperature, and analysis of the plot indicates an approximate gelation temperature. A 4 centimeter flat, steel spindle is attached to the rotor of the rheometer and the calibration routine is carried out to calibrate the spacing between the rheometer Peltier plate and the spindle. An increase in temperature from 20° C. to 100° C. (68° F. to 212° F.) at a rate of 0.1° C. (0.18° F.) per second with a constant shear rate of 5 sec-1 is programmed into the rheometer software. A 2 gram sample of plastisol is loaded onto the Peltier plate and the program is initiated. At the conclusion of the temperature ramp, the results are plotted as output of viscosity versus temperature on a semi-Log chart to produce a gel curve. Then, lines are hand-drawn asymptotically to the two sections of the gel curve, extending them toward the X axis until they intersect. The gel temperature is then approximated by noting the temperature corresponding to the intersection of the hand-drawn lines.

Heat Loss—The Heat Loss test is applied to fused plastisols to determine the percent loss of mass during heat aging. Low heat loss is desirable, as volatilized plasticizer can contaminate nearby surfaces, such as windshield interiors on new cars. Fused sheets of plastisol are prepared substantially as in the Heat Stability Test. Square samples (5.0 cm by 5.0 cm (2 inch by 2 inch)) are punched or cut and weighed to +/−0.0001 g. The samples are incubated in an 82° C. (180° F.) oven for 7 and/or 14 days, and cooled for 30 minutes before re-weighing. The heat loss is expressed as a percentage of the original weight of the sample.

Plasticizer Volatility—The Plasticizer Volatility test is used to determine the relative plasticizer volatility that may affect plastisol processing. Lower plasticizer volatility is desired, especially for compounded (extruded) plastisols. A 1-gram sample of plasticizer is accurately weighed (+/−0.0001 g) and incubated in an oven for 3 minutes at 204° C. (400° F.). The weight loss is determined and the percentage of weight loss is reported as plasticizer volatility.

Exudation Test—Fused plastisol discs are made in aluminum weighing dishes using from 15+/−0.5 grams of liquid plastisol. Three discs per plastisol sample are prepared. The plastisols are fused for ten minutes in an oven preheated to 400° F. The discs are cooled quickly in water and removed from the aluminum dishes. To determine exudation, a stack of two fused plastisol discs is incubated in a 180° F. oven for at least 4 weeks. The discs are examined after 24 hours and weekly for at least four weeks and compared with an identical reference strip kept at room temperature. The visible presence of exudation is noted, and the amount exuded is determined by visual inspection. Exudation values are assigned as falling into one of the following ranges: trace-light-moderate-heavy.

Results of several of the various tests are reported in Table 1 below. The Control EMS PVC composition gave a gel temperature of 55 degrees Celsius, as did the PVC composition made from the EMS of Example 1, while the PVC composition made from the EMS of Example 3 gave a gel temperature of 53 degrees Celsius. No exudation was seen for any of the PVCs, after 24 hours, 1 week and 2 weeks both at room temperature and at 180 degrees Fahrenheit, and Metrastat heat stabilities were likewise very similar in ranging from colorless to at most a lemon yellow color:

TABLE 1

|  | Control | Ex. 1 | Ex. 3 |
| --- | --- | --- | --- |
| Air Release | Good | Good | Good |
| Hardness (Shore A) | 70 | 70 | 70 |
| Heat Loss @ 180° F. (%), 7 Day | 9.0% | 9.3% | 8.1% |
| Heat Loss @ 180° F. (%), 14 Day | 11.9% | 11.8% | — |
| Plasticizer Volatility (% loss) (3 min @ 400° F.) | 13.3% | 10.2% | 11.3% |
| Brookfield RV Viscosity |  |  |  |
| Spindle | 3 | 3 | 3 |
| Initial @ 20 rpm, cps | 975 | 1075 | 985 |
| Initial @ 2 rpm, cps | 1,150 | 1450 | 1200 |
| Spindle | 3 | 3 | 3 |
| 1 Day @ 20 rpm, cps | 1780 | 1765 | 2,000 |
| 1 Day @ 2 rpm, cps | 2200 | 2300 | 2500 |
| Spindle | 3 | 3 | 3 |
| 2 Day @ 20 rpm, cps | 2325 | 2385 | 2525 |
| 2 Day @ 2 rpm, cps | 3300 | 3700 | 3300 |
| Spindle | 4 | 4 | 3 |
| 7 Day @ 20 rpm, cps | 4230 | 4400 | 4370 |
| 7 Day @ 2 rpm, cps | 6500 | 6700 | 5750 |
| Spindle | 4 | 4 | 4 |
| 14 Day @ 20 rpm, cps | 7150 | 7320 | 6590 |
| 14 Day @ 2 rpm, cps | 11300 | 11600 | 9600 |

The invention claimed is:
1. A process for making an epoxidized fatty acid ester from an epoxidized natural fat or oil, comprising:
   determining the moisture content of one or more epoxidized natural fats or oils;

selecting a low moisture epoxidized natural fat or oil for use;

transesterifying the selected low moisture natural fat or oil with an anhydrous alcohol in the presence of a transesterification catalyst selected from the group consisting of sodium methoxide, sodium ethoxide, potassium methoxide, potassium ethoxide, potassium tert-butoxide or an N-heterocyclic carbene catalyst and under conditions which are effective for carrying out the transesterification reaction;

allowing the products of the transesterification reaction to phase-separate into a byproduct glycerol-containing phase and epoxidized fatty acid ester-containing phase; and recovering the epoxidized fatty acid ester-containing phase, under the circumstance that the above process steps are carried out in the substantial absence of moisture from other sources than the selected low moisture epoxidized natural fat or oil.

2. The process of claim 1, wherein the selected low moisture epoxidized natural fat or oil is characterized by a moisture content of 0.5 percent by weight or less when combined with the alcohol for carrying out the transesterification reaction.

3. The process of claim 2, wherein the moisture content is 0.25 percent by weight or less.

4. The process of claim 3, wherein the moisture content is 0.1 percent by weight or less.

5. A process for making an epoxidized fatty acid ester from an epoxidized natural fat or oil, comprising:

making a low moisture epoxidized natural fat or oil feedstock;

transesterifying the low moisture natural fat or oil with an anhydrous alcohol in the presence of a transesterification catalyst selected from the group consisting of sodium methoxide, sodium ethoxide, potassium methoxide, potassium ethoxide, potassium tert-butoxide or an N-heterocyclic carbene catalyst and under conditions which are effective for carrying out the transesterification reaction;

allowing the products of the transesterification reaction to phase-separate into a byproduct glycerol-containing phase and epoxidized fatty acid ester-containing phase; and recovering the epoxidized fatty acid ester-containing phase, under the circumstance that the above process steps are carried out in the substantial absence of moisture from other sources than the low moisture epoxidized natural fat or oil.

6. The process of claim 5, wherein making the low moisture epoxidized natural fat or oil feedstock comprises drying one or more epoxidized natural fats and oils.

7. The process of claim 5, wherein making the low moisture epoxidized natural fat or oil feedstock comprises blending two or more of the epoxidized natural fats and oils having higher and lower moisture contents, to achieve a blended low moisture epoxidized natural fat or oil feedstock.

8. The process of claim 5, wherein the low moisture epoxidized natural fat or oil is characterized by a moisture content of 0.5 percent by weight or less when combined with the alcohol for carrying out the transesterification reaction.

9. The process of claim 8, wherein the moisture content is 0.25 percent by weight or less.

10. The process of claim 9, wherein the moisture content is 0.1 percent by weight or less.

* * * * *